(12) United States Patent
Benner et al.

(10) Patent No.: US 9,062,336 B1
(45) Date of Patent: Jun. 23, 2015

(54) RECOMBINASE-BASED AMPLIFICATION WITH SUBSTITUTE NUCLEOTIDES

(71) Applicants: Steven A Benner, Gainesville, FL (US); Nidhi Sharma, Gainesville, FL (US)

(72) Inventors: Steven A Benner, Gainesville, FL (US); Nidhi Sharma, Gainesville, FL (US)

( * ) Notice: Subject to any disclaimer, the term of this patent is extended or adjusted under 35 U.S.C. 154(b) by 133 days.

(21) Appl. No.: 13/789,022

(22) Filed: Mar. 7, 2013

(51) Int. Cl.
*C12P 19/34* (2006.01)

(52) U.S. Cl.
CPC ..................................... *C12P 19/34* (2013.01)

(58) Field of Classification Search
CPC ...................................................... C12P 19/34
USPC ........................................................ 435/91.2
See application file for complete search history.

(56) References Cited

PUBLICATIONS

Piepenburg et al., DNA detection using recombination proteins. PLoA Biology, 4 (7( doi:10.1371/journal.pbio.0040204.
Hoshika et al., Artificial genetic systems. Self-avoiding DNA in PCR and multiplexed PCR. Angew. Chem. Int Edit., 49, 5554-5557.
Yang et al., Amplification, mutation, and sequencing of a six-letter synthetic genetic system. J. Am. Chem. Soc., 133, 15105-15112.

*Primary Examiner* — Ardin Marschel (57) ABSTRACT

This invention covers methods for isothermal amplification of DNA. It is based on the unexpected discovery that primers having, at some positions, adenine substituted by 2-aminopurine or diaminopurine, guanine by inosine, thymine by 2-thiothymine, and cytosine by N4-ethylcytosine ("substituted primers") were accepted by enzymes used in the standard recombinase polymerase assay (RPA). Further unexpected was the discovery that target nucleotides are efficiently amplified in an RPA-like process (hereinafter abbreviated as simply RPA) using substituted primers. RPA-like processes were also discovered to amplify target DNA with substituted primers tagged with oligonucleotides incorporating nucleotides from an artificially expanded genetic information system (AEGIS).

3 Claims, 5 Drawing Sheets

X = N or CH   R = electron withdrawing group

Figure 5

RECOMBINASE-BASED AMPLIFICATION WITH SUBSTITUTE NUCLEOTIDES

STATEMENT REGARDING FEDERALLY SPONSORED RESEARCH OR DEVELOPMENT

This invention was made with government support under a grant awarded by the United States Defense Advanced Research Project Agency (R0011-11-2-0018). The government has certain rights in the invention.

CROSS REFERENCE TO RELATED APPLICATIONS

None

THE NAMES OF THE PARTIES TO A JOINT RESEARCH AGREEMENT

Not applicable

INCORPORATION-BY-REFERENCE OF MATERIAL SUBMITTED ON A COMPACT DISC

None

BACKGROUND OF THE INVENTION (1) Field of the Invention

The field of this invention is nucleic acid chemistry, more specifically nucleic acid amplification technology, and more specifically isothermal amplification methods. This invention relates to processes that, without raising or lowering the temperature, increase the number of copies ("amplify") of a specific "target" DNA or RNA (collectively xNA) sequence.

(2) Description of Related Art

For practical applications in many areas, including the research and DNA- and RNA-targeted diagnostics, methods that amplify nucleic acids without the need to do temperature cycling are highly desirable. Many such "isothermal amplification" methods are known in the art, including those known as "recombinase polymerase amplification" (RPA) [Piepenburg, O., Williams, C. H., Stemple, D. L., Armes, N. A. (2006) DNA Detection Using Recombination Proteins. *PLoS Biol* 4 (7): e204. doi:10.1371/journal.pbio.0040204. PMC 1475771. PMID 16756388.], rolling circle amplification (RCA), helicase-dependent amplification (HDA), NASBA, and LAMP, among others Isothermal amplification methods frequently do not perform well, however. In many cases, the extent of amplification appears to depend on the specific sequence being amplified or (perhaps) the sequence of probes and/or primers used in the amplification. In some cases, the amplification fails entirely. When the amplification targets more than one target nucleic acid species, isothermal amplification methods often fail.

Essentially no theory explains these and other variable results, although speculation can be found in the public and private art, some of it contradictory, other examples being informal. Without any attempt to be exhaustive, speculative suggestions include the possibility that at low temperatures, non-Watson Crick interactions might cause some of the DNA molecules involved (primer, probe, or analyte) to fold in a way that defeats the amplification process. Others have suggested that high temperatures must be regularly traversed to avoid an (often unknown) intra- or intermolecular interaction from capturing the system as an artifact. Primer-primer interactions have been invoked to explain failure of various isothermal amplification systems, especially when is multiplexing is attempted.

None of these explanations are established. Few data allow us to prefer one over the other. As a consequence, the art contains no clear guidance as to what experiments might be tried to overcome these problems, and to generate reliable procedures of performing isothermal amplification for all target sequences and, especially, for multiple (more than one) target sequences.

BRIEF SUMMARY OF THE INVENTION

This invention is based on the unexpected discovery that primers ("substituted primers") in which at least some of the A, T, G, and C nucleobases are substituted at some (but not necessarily all) sites (positions) with analogs designated A*, T*, G* and C*, by enzymes that work in the standard recombinase polymerase assay (RPA) known in the art [Piepenburg et al., op. cit.]. The preferred substitutions replace adenine by 2-aminopurine or diaminopurine, replace guanine by inosine, replace thymine by 2-thiothymine, and replace cytosine by N4-ethylcytosine. This invention is further based on the unexpected discovery that target nucleotides are indeed amplified in an RPA-like process (hereinafter abbreviated as simply RPA) using these substituted primers. Further, this invention is based on the discovery that RPA-like processes where its substituted primers are tagged with oligonucleotides incorporating nucleotides selected from as artificially expanded genetic information system (AEGIS, herein defined) also perform well.

DETAILED DESCRIPTION OF THE INVENTION

1. Narrative

For application, oligonucleotides were synthesized by solid phase automated synthesis, as described in the following two references, which are incorporated in their entirety herein.

Hoshika, S., Leal, N., Chen, F., Benner, S. A. (2010) Artificial genetic systems. Self-avoiding DNA in PCR and multiplexed PCR. *Angew. Chem. Int. Edit.* 49, 5554-5557

Yang, Z., Chen, F., Alvarado, J. B., Benner, S. A. (2011) Amplification, mutation, and sequencing of a six-letter synthetic genetic system. *J. Am. Chem. Soc.* 133, 15105-15112

The examples show that sequences of DNA chosen from viral targets (influenza and HIV, presented as short DNA segments that simulated the live RNA viruses) can be isothermally amplified using an RPA-like architecture and substituted primers. For this purpose, a commercially available RPA kit was purchased from TwistDx. Visualization of the isothermal amplification products was done by Agarose gel electrophoresis.

The sequences of the amplimers and the primers are shown in Table 1. Standard nucleotides are indicated by G, A, C, and T. Substituted nucleotides are indicated by G*, A*, C*, and T*, respectively. These examples target a region of the influenza A virus (in its DNA form) and the Gag region of HIV (also in its DNA form).

TABLE 1

| | Amplimer |
|---|---|
| Influenza A SEQ ID 1 | CTTGAGGCTCTCATGGAATGGCTAAAGACAAGACC AATCCTGTCACCTCTGACTAAGGGGATTTTGGGGTT TGTGTTCACGCTCACCGTGCCCAGTGAGCGAGGACT GCAGCGTAGACGCTTTGTCCAAAATG |
| HIV-gag SEQ ID 2 | GGACAtCAaGCAGCcATGCAAATGTTAAAAGAgaccatc aatgaggaagctgcagactgggataggttacatccagtgcatgcagggccaattcc accagGCCAGATGAGaGAACCAAGGGGAAGTGACA TAGCA |

TABLE 2

| | Sequence |
|---|---|
| Flu-RPA3-Fp1 SEQ ID 3 | CTTGAGGCTCTCATGGAATGGCTAAAGACAAGACC |
| Flu-RPA3-SA-Fp1 SEQ ID 4 | CTTGAGGCTCTCATGGAATGGCTAAAGACAA*G*A*C*C |
| Flu-RPA3-AESA-Fp1 SEQ ID 5 | CTA PTC CPC CAP CPA PC CTTGAGGCTCTCATGGAATGGCTAAAGACAA*G*A*C*C |
| Flu-RPA3-Rp1 SEQ ID 6 | CATTTTGGACAAAGCGTCTACGCTGCAGTCC |
| Flu-RPA3-SA-Rp1 SEQ ID 7 | CATTTTGGACAAAGCGTCTACGCTGCA*G*T*C*C |
| Flu-RPA3-AESA-Rp1 SEQ ID 8 | CAG PAA GPG GTP GPT PG CATTTTGGACAAAGCGTCTACGCTGCA*G*T*C*C |
| HIV-gag-FP1 SEQ ID 9 | GGACAtCAaGCAGCcATGCAaATGTTAAAAGAG |
| HIV-gag-SA-FP1 SEQ ID 10 | GGACAtCAaGCAGCcATGCAaATGTTAAA*A*G*A*G |
| HIV-gag-AESA-FP1 SEQ ID 11 | CTA PTC CPC CAP CPA PC GGA CAt CAa GCA GCc ATG CAa ATG TTA AA*A* G*A*g |
| HIV-gag-RP1 SEQ ID 12 | TGCTATGTCACTTCCCCTTGGTTCTCTCATCTGGC |
| HIV-gag-SA-RP1 SEQ ID 13 | TGCTATGTCACTTCCCCTTGGTTCTCTCATC*T*G*G*C |
| HIV-gag-AESA-RP1 SEQ ID 14 | CAG PAA GPG GTP GPT PG TGC TAT GTC ACT TCC CCT TGG TTC TCT CAT C*T*G* G*C |

EXAMPLES

Example 1

Jump Start Reaction to Generate Double Stranded Target DNA

In this example, we prepared the target molecules to test RPA-like isothermal amplification of influenza and HIV sequences with substituted primers.

Single-stranded amplimers containing only standard nucleobases were obtained from Integrated DNA Technologies (IDT, Coralville Iowa). The target DNA was introduced in double-stranded form. This was prepared by PCR amplification using the standard primers (Table 2) and single stranded amplimer (Table 1) using Jump Start polymerase and the following recipe.

Figure 1:
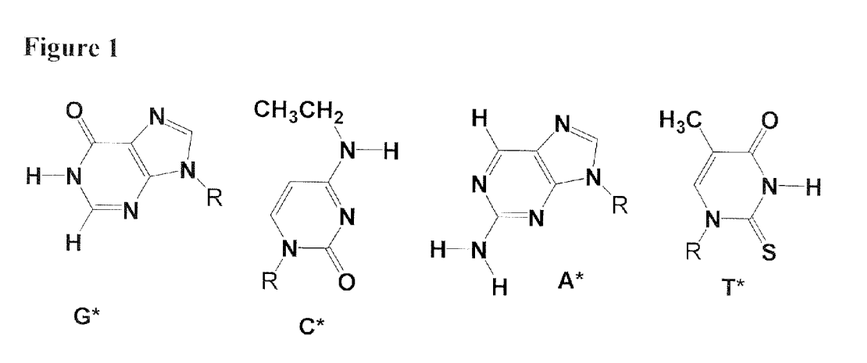
FIG. 1. The presently preferred nucleobases analogs that substitute for G, C, A, and T in the substituted primers, where R is the point of attachment to the oligonucleotide.
Figure 2:
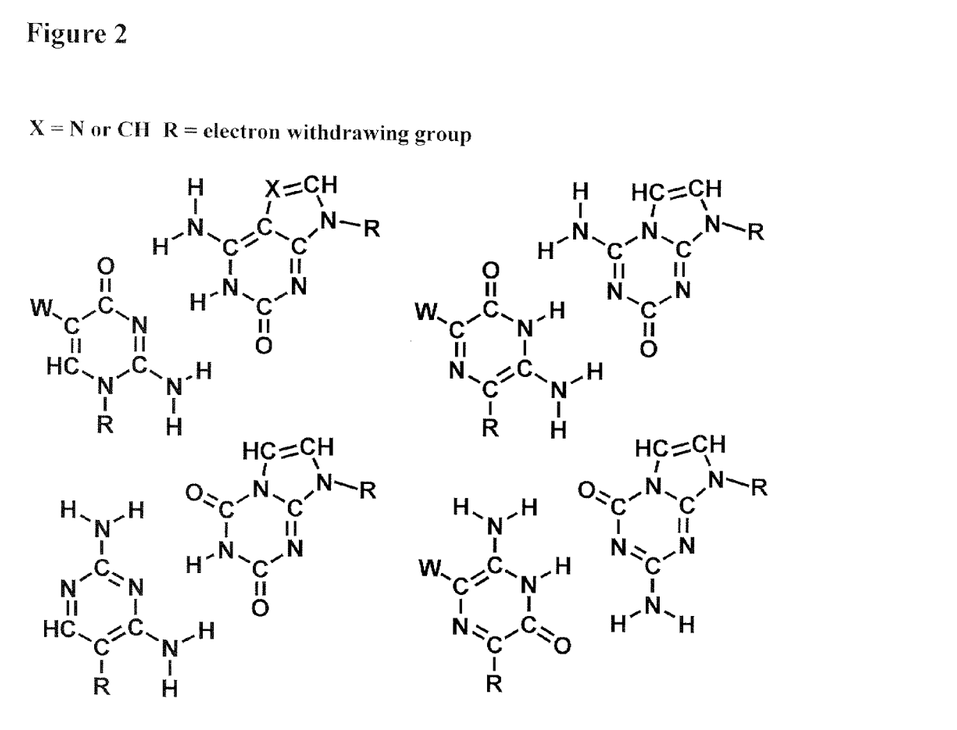
FIG. 2. The presently preferred components selected from an artificially expanded genetic information system, where R is the point of attachment to the oligonucleotide, and W is an electron withdrawing group such as nitro or cyano.
Figure 3:
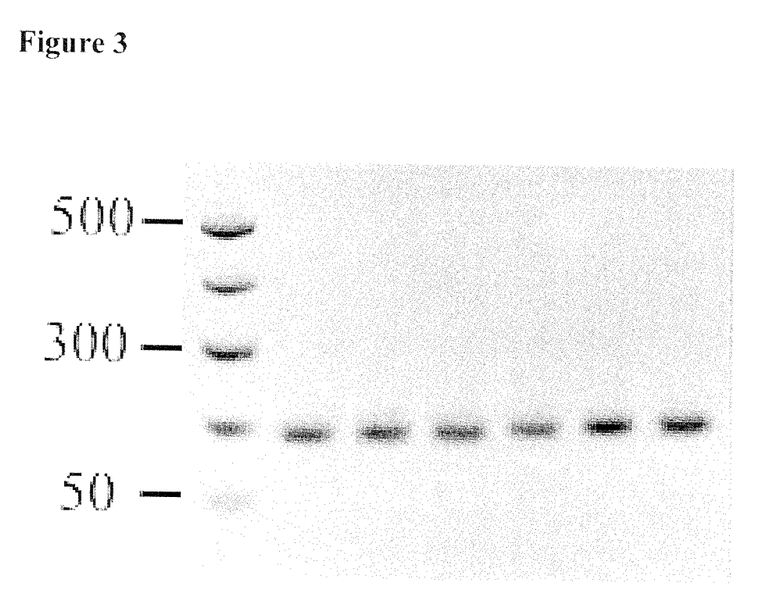
FIG. 3. Data from Example 1.

A PCR (total volume 50 μL) was performed in Jumpstart buffer (Sigma 1×, 10 mM Tris-HCl, pH 8.3 at 25° C., 50 mM KCl, 1.5 mM MgCl$_2$, and 0.001% gelatin) with the indicated forward and reverse primers (0.25 μM) and dNTPs (0.2 mM), Jumpstart Taq DNA polymerase (0.02 units) and the single-stranded amplimer (0.1 μM). Additional MgCl$_2$ (1 mM) was added to the reaction. The mixture was incubated in a thermal cycler at 95° C. for 1 min, followed by 35 cycles at 95° C. for 30 sec; 56° C. or 60° C. for 30 sec and 72° C. for 1 min, with a final extension at 72° C. for 5 min. The reactions were run in triplicate, and the products were recovered using PCR cleanup columns and used in RPA reactions. The results are shown in FIG. 3.

Example 2

Quantitation of DNA

A solution of DNA (1 μL) was prepared in distilled water (100 μL) and its absorbance at 260 nm ($A_{260}$) was measured. For influenza A as a target, the $A_{260}$ was 0.010. With an extinction coefficient of 50, this corresponds to 50 ng of DNA/μL. For HIV as a target, the $A_{260}$ was 0.009 after a 1/200 dilution, and the PCR product was quantitated to be 90 ng/μL. To decrease the number of copies of the template to ~1000, each of the samples was diluted 100,000 fold. The reactions were set up as described above and incubated at 38° C.

Setting Up the RPA (Control) and RPA-Like Reactions

Reactions were targeted to amplify 1 μL of PCR product after dilution, as follows:

Control reaction: A 1/10 dilution of the control DNA (provided in the kit from TwistDx) was made. The reaction was setup as follows:

1. A 1/10 dilution of the positive control DNA was prepared (10 μL, in dH$_2$O).
2. Primer solution (8 μL) was added to a fresh 1.5 ml micro centrifuge tube.
3. Then added was 29.5 μL of rehydration buffer to the primer solution. The mixture was briefly vortexed and spun.
4. Then added was 10 μL of the diluted positive control DNA to the solution. The mixture was briefly vortexed and spun.
5. This mixture was added to a freeze-dried TwistAmp™ "Basic Reaction Pellets" (TwistDx). These contain polymerases and other components required for the classical RPA reaction, and are mixed with the solution by pipetting up and down until the entire pellet was suspended.
6. The reaction was started by adding 2.5 μL 280 mM of magnesium acetate, followed by thorough by vortexed. The tubes were placed in the heating block (38° C.) and incubated for 4 minutes.
7. After 4 minutes, samples were vortexed and returned to the block.
8. The incubation was continues for 40 minutes.

The following were used as Test Reactions:

1. Mixtures containing target influenza DNA and primers, and primers alone were set up as described above. Forward and reverse primers built with standard nucleotides were added (2.4 μt), followed by 29.5 μL rehydration buffer.
2. Water was added to each tube to make the total reaction volume ~47.5 μL.
3. The tubes were vortexed and the reaction mixture was transferred to the TwistAmp™ Basic Reaction Pellets. This was transferred back to the 1.5 mL eppendorf tubes.
4. 2.5 μL of 280 mM of magnesium acetate was added to the cap of the tube. The tubes were vortexed, centrifuged and immediately transferred to a heating block (38° C.) and incubated for 4 minutes.
5. After 4 minutes, samples were vortexed and returned to the block.

6. Continued the incubation for 40 minutes.

Figure 4:
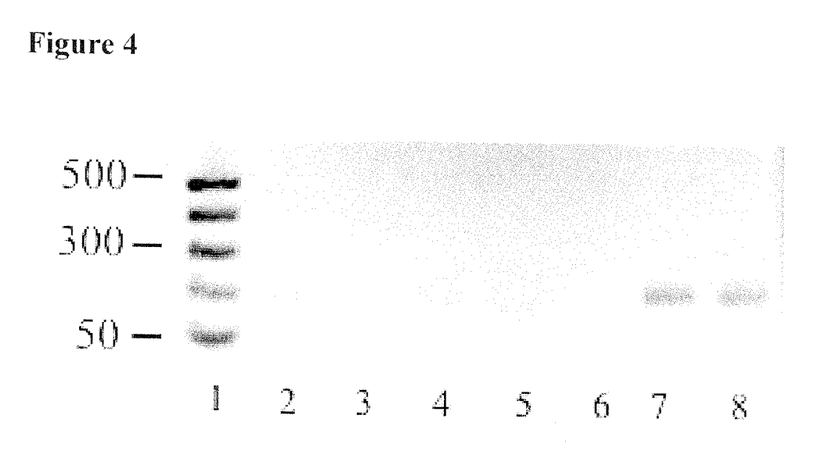
FIG. 4. Data from Example 2.

The results are shown in FIG. 4. At the end of 40 minutes incubation, the samples were diluted 4 fold and extracted by using phenol:chloroform to remove all proteins (recommended by manufacturer) as the recombinant proteins and polymerase in the reaction retard the migration of the amplified DNA. The extracted samples were ethanol precipitated with sodium acetate (3M, 1/10$^{th}$) and incubated overnight at −20° C.

The samples were resuspended in water and run on a 2.5% agarose gel. As seen in FIG. 4, control DNA is amplified with control primers (Lane 2). No signal is obtained in Lane 3 in the absence of magnesium acetate. With influenza target DNA and standard primers, faint bands were observed in both the presence and absence of target influenza DNA (Lanes 4 and 5). With HIV target DNA, signal was not observed in the absence of magnesium acetate (Lane 6), however, distinct bands were observed in the presence and absence of target HIV DNA (Lanes 7 and 8).

Experiment 3: RPA-Like Amplifications with SAMRS and AEGIS-SAMRS Hybrid Primers

A master mix containing forward and reverse primers (2.4 µL each, 480 nM final concentrations) was reconstituted in rehydration buffer (provided by TwistDx), as follows:
Primer F (standard, SAMRS or AEGIS-SAMRS oligonucleotides): 2.4 µL
Primer R (standard, SAMRS or AEGIS-SAMRS oligonucleotides): 2.4 µL
Rehydration buffer: 29.5 µL
Water: 11.2 µL This was placed into pre-prepared tubes (TwistDx) containing the freeze dried RPA pellets, which contain polymerases and other components required for the classical RPA reaction. Then, aliquots (22.75 µL) were transferred to two TwistDx Eppendorf tubes to set up positive reactions and negative control. To create the positive, target DNA template (0.8 µL) was added to one aliquot. Water in equal amounts was added to the other aliquots to create the negative control. To create a reference standard for subsequent gel electrophoresis, DNA solution (0.8 µL) was diluted into water lacking primers and magnesium acetate. For reactions supported by AEGIS-SAMRS primers, dZTP (20 µM) was added. The mixtures were then incubated at 38° C.

Figure 5:
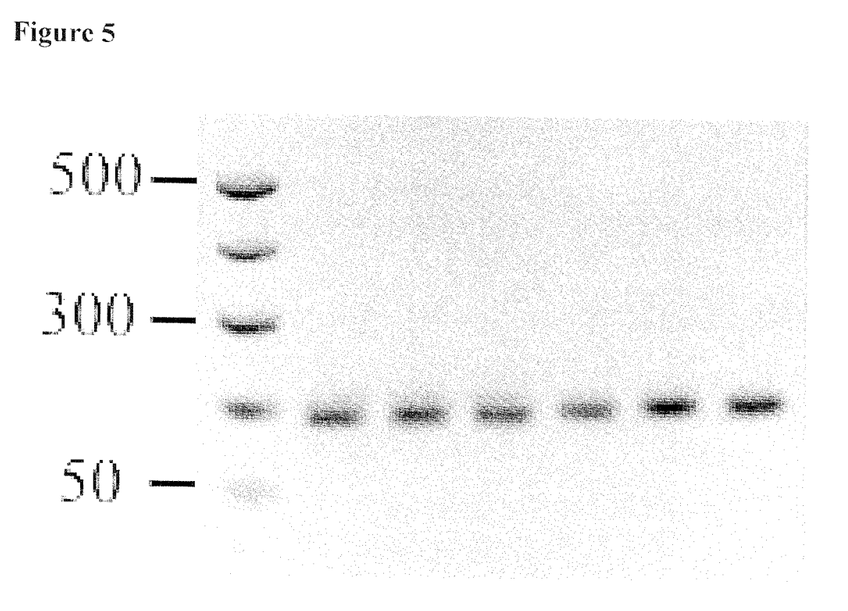
FIG. 5. Data from Example 3.

The results are shown in FIG. 5. As seen in the experiment with the Influenza A target, a product was obtained using standard primers as a faint band following electrophoresis on an agarose gel (2.5%) stained with ethidium bromide (lane 2). The bands in lane 3 were assigned to the primers and their dimers, as target was absent in the reaction mixture.

With the influenza A DNA target, the primers with SAMRS modifications gave a stronger and more clearly defined product band having the size expected for the amplification product (lane 4). In the absence of target, only diffuse product were seen (lane 5). With the AEGIS-SAMRS hybrid primers, the only product observed was a well-defined band having the expected size (lane 6). The slower electrophoretic mobility indicates that the external AEGIS segments of the primers were also copied. No signal was seen in the negative control (lane 7), which contained AEGIS-SAMRS primers alone. This suggests that the presence of SAMRS and AEGIS-SAMRS nucleotides in the primers prevents the artifacts and allows for the reactions to be efficient in presence of a target. The HIV gag DNA target gave a good product signal with the standard primers (lane 2). A diffuse product is for primer alone (lane 3). With the SAMRS primers and DNA target (lane 4), a clear and directly sized product is seen; the second band may arise from excess template. The results with SAMRS primer alone are shown in lane 5. However, with the reaction with AEGIS-SAMRS primers and target DNA alone, only a single product having the correct size is seen (lane 6), and no background is seen with the AEGIS-SAMRS primers alone (lane 7).

The results were confirmed using a Luminex assay, with probes attached to beads targeted to regions near the center of the amplicon.

What is claimed is:

1. A process for amplifying the two complementary DNA strands in a DNA target duplex, wherein said process comprises:
   (a) contacting in buffered aqueous solution said DNA target duplex with a Basic Reaction Pellet comprising a polymerase, a recombinase, and all other components necessary to support a Recombinase Polymerase Amplification, together with
   (b) a solution containing any 2'-deoxynucleoside triphosphates that are required to complement each and every nucleotide in the said complementary DNA sequences and substituted primers, where
   (c) said substituted primers comprise a first primer that is substantially complementary in sequence to a segment at or near the 3'-end of the first of said DNA strands, and a second primer that is substantially complementary in sequence to a segment at or near the 3'-end of the second of said DNA strands, and where
   (d) within said substituted primer at least one adenine in at least one of its adenosine nucleotides is substituted by 2-aminopurine or diaminopurine, at least one guanine in at least one of its guanosine nucleotides is substituted by inosine, at least one thymine is substituted by 2-thiothymine, and at least one cytosine is substituted by N4-ethylcytosine, and wherein
   (e) the total number of said substitutions is at least four.

2. The process of claim 1 wherein appended to the 5'-end of one or more of said substituted primers is a tag that comprises a preselected oligonucleotide that contains at least one nucleotide selected from the group consisting of wherein X is selected from the group consisting on N and CH, W is nitro, cyano, or another electron withdrawing group, and R is the appoint of attachment of the indicated heterocycle to the oligonucleotide.

3. The process of claim 2, wherein said preselected oligonucleotide contains at least one nucleotide selected from the group consisting of and and R is the appoint of attachment of the indicated heterocycle to the oligonucleotide.

* * * * *

SEQUENCE LISTING

<160> NUMBER OF SEQ ID NOS: 14

<210> SEQ ID NO 1
<211> LENGTH: 133
<212> TYPE: DNA
<213> ORGANISM: Artificial Sequence
<220> FEATURE:
<223> OTHER INFORMATION: Synthetic

<400> SEQUENCE: 1
cttgaggctc tcatggaatg gctaaagaca agaccaatcc tgtcacctct          50
gactaagggg attttggggt ttgtgttcac gctcaccgtg cccagtgagc         100
gaggactgca gcgtagacgc tttgtccaaa atg                           133

<210> SEQ ID NO 2
<211> LENGTH: 135
<212> TYPE: DNA
<213> ORGANISM: Artificial Sequence
<220> FEATURE:
<223> OTHER INFORMATION: Synthetic

<400> SEQUENCE: 2
ggacatcaag cagccatgca aatgttaaaa gagaccatca atgaggaagc          50
tgcagactgg gataggttac atccagtgca tgcagggcca attccaccag         100
gccagatgag agaaccaagg ggaagtgaca tagca                         135

```
<210> SEQ ID NO 3
<211> LENGTH: 35
<212> TYPE: DNA
<213> ORGANISM: Artificial Sequence
<220> FEATURE:
<223> OTHER INFORMATION: Synthetic

<400> SEQUENCE: 3
cttgaggctc tcatggaatg gctaaagaca agacc                                  35

<210> SEQ ID NO 4
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (31)..(31)
<223> OTHER INFORMATION: n = a nonstandard nucleotide of the instant
      invention
<220> FEATURE:
<221> NAME/KEY: misc_feature
<222> LOCATION: (32)..(32)
<223> OTHER INFORMATION: n = a nonstandard nucleotide of the instant
      invention
<220> FEATURE:
<221> NAME/KEY: misc_feature
<222> LOCATION: (33)..(33)
<223> OTHER INFORMATION: n = a nonstandard nucleotide of the instant
      invention
<220> FEATURE:
<221> NAME/KEY: misc_feature
<222> LOCATION: (34)..(34)
<223> OTHER INFORMATION: n = a nonstandard nucleotide of the instant
      invention

<400> SEQUENCE: 4
cttgaggctc tcatggaatg gctaaagaca nnnnc                                  35

<210> SEQ ID NO 5
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: n = a nonstandard nucleotide of the instant
      invention
<220> FEATURE:
<221> NAME/KEY: misc_feature
<222> LOCATION: (8)..(8)
<223> OTHER INFORMATION: n = a nonstandard nucleotide of the instant
      invention
<220> FEATURE:
<221> NAME/KEY: misc_feature
<222> LOCATION: (12)..(12)
<223> OTHER INFORMATION: n = a nonstandard nucleotide of the instant
      invention
<220> FEATURE:
<221> NAME/KEY: misc_feature
<222> LOCATION: (14)..(14)
<223> OTHER INFORMATION: n = a nonstandard nucleotide of the instant
      invention
<220> FEATURE:
<221> NAME/KEY: misc_feature
<222> LOCATION: (16)..(16)
<223> OTHER INFORMATION: n = a nonstandard nucleotide of the instant
      invention
<220> FEATURE:
<221> NAME/KEY: misc_feature
```

<222> LOCATION: (48)..(48)
<223> OTHER INFORMATION: n = a nonstandard nucleotide of the instant
      invention
<220> FEATURE:
<221> NAME/KEY: misc_feature
<222> LOCATION: (49)..(49)
<223> OTHER INFORMATION: n = a nonstandard nucleotide of the instant
      invention
<220> FEATURE:
<221> NAME/KEY: misc_feature
<222> LOCATION: (50)..(50)
<223> OTHER INFORMATION: n = a nonstandard nucleotide of the instant
      invention
<220> FEATURE:
<221> NAME/KEY: misc_feature
<222> LOCATION: (51)..(51)
<223> OTHER INFORMATION: n = a nonstandard nucleotide of the instant
      invention

<400> SEQUENCE: 5
ctantccncc ancnancctt gaggctctca tggaatggct aaagacannn nc            52

<210> SEQ ID NO 6
<211> LENGTH: 31
<212> TYPE: DNA
<213> ORGANISM: Artificial Sequence
<220> FEATURE:
<223> OTHER INFORMATION: Synthetic

<400> SEQUENCE: 6
cattttggac aaagcgtcta cgctgcagtc c                                  31

<210> SEQ ID NO 7
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (27)..(27)
<223> OTHER INFORMATION: n = a nonstandard nucleotide of the instant
      invention
<220> FEATURE:
<221> NAME/KEY: misc_feature
<222> LOCATION: (28)..(28)
<223> OTHER INFORMATION: n = a nonstandard nucleotide of the instant
      invention
<220> FEATURE:
<221> NAME/KEY: misc_feature
<222> LOCATION: (29)..(29)
<223> OTHER INFORMATION: n = a nonstandard nucleotide of the instant
      invention
<220> FEATURE:
<221> NAME/KEY: misc_feature
<222> LOCATION: (30)..(30)
<223> OTHER INFORMATION: n = a nonstandard nucleotide of the instant
      invention

<400> SEQUENCE: 7
cattttggac aaagcgtcta cgctgcnnnn c                                  31

<210> SEQ ID NO 8
<211> LENGTH: 48
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: n = a nonstandard nucleotide of the instant
      invention -continued

```
<220> FEATURE:
<221> NAME/KEY: misc_feature
<222> LOCATION: (8)..(8)
<223> OTHER INFORMATION: n = a nonstandard nucleotide of the instant
      invention
<220> FEATURE:
<221> NAME/KEY: misc_feature
<222> LOCATION: (12)..(12)
<223> OTHER INFORMATION: n = a nonstandard nucleotide of the instant
      invention
<220> FEATURE:
<221> NAME/KEY: misc_feature
<222> LOCATION: (14)..(14)
<223> OTHER INFORMATION: n = a nonstandard nucleotide of the instant
      invention
<220> FEATURE:
<221> NAME/KEY: misc_feature
<222> LOCATION: (16)..(16)
<223> OTHER INFORMATION: n = a nonstandard nucleotide of the instant
      invention
<220> FEATURE:
<221> NAME/KEY: misc_feature
<222> LOCATION: (44)..(44)
<223> OTHER INFORMATION: n = a nonstandard nucleotide of the instant
      invention
<220> FEATURE:
<221> NAME/KEY: misc_feature
<222> LOCATION: (45)..(45)
<223> OTHER INFORMATION: n = a nonstandard nucleotide of the instant
      invention
<220> FEATURE:
<221> NAME/KEY: misc_feature
<222> LOCATION: (46)..(46)
<223> OTHER INFORMATION: n = a nonstandard nucleotide of the instant
      invention
<220> FEATURE:
<221> NAME/KEY: misc_feature
<222> LOCATION: (47)..(47)
<223> OTHER INFORMATION: n = a nonstandard nucleotide of the instant
      invention

<400> SEQUENCE: 8
cagnaagngg tngntngcat tttggacaaa gcgtctacgc tgcnnnnc                    48

<210> SEQ ID NO 9
<211> LENGTH: 33
<212> TYPE: DNA
<213> ORGANISM: Artificial Sequence
<220> FEATURE:
<223> OTHER INFORMATION: Synthetic

<400> SEQUENCE: 9
ggacatcaag cagccatgca aatgttaaaa gag                                    33

<210> SEQ ID NO 10
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(29)
<223> OTHER INFORMATION: n = a nonstandard nucleotide of the instant
      invention
<220> FEATURE:
<221> NAME/KEY: misc_feature
<222> LOCATION: (30)..(30)
<223> OTHER INFORMATION: n = a nonstandard nucleotide of the instant
      invention
<220> FEATURE:
<221> NAME/KEY: misc_feature
<222> LOCATION: (31)..(31)
<223> OTHER INFORMATION: n = a nonstandard nucleotide of the instant
      invention
```

```
<220> FEATURE:
<221> NAME/KEY: misc_feature
<222> LOCATION: (32)..(32)
<223> OTHER INFORMATION: n = a nonstandard nucleotide of the instant
      invention

<400> SEQUENCE: 10
ggacatcaag cagccatgca aatgttaann nng                                   33

<210> SEQ ID NO 11
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: n = a nonstandard nucleotide of the instant
      invention
<220> FEATURE:
<221> NAME/KEY: misc_feature
<222> LOCATION: (8)..(8)
<223> OTHER INFORMATION: n = a nonstandard nucleotide of the instant
      invention
<220> FEATURE:
<221> NAME/KEY: misc_feature
<222> LOCATION: (12)..(12)
<223> OTHER INFORMATION: n = a nonstandard nucleotide of the instant
      invention
<220> FEATURE:
<221> NAME/KEY: misc_feature
<222> LOCATION: (14)..(14)
<223> OTHER INFORMATION: n = a nonstandard nucleotide of the instant
      invention
<220> FEATURE:
<221> NAME/KEY: misc_feature
<222> LOCATION: (16)..(16)
<223> OTHER INFORMATION: n = a nonstandard nucleotide of the instant
      invention
<220> FEATURE:
<221> NAME/KEY: misc_feature
<222> LOCATION: (46)..(46)
<223> OTHER INFORMATION: n = a nonstandard nucleotide of the instant
      invention
<220> FEATURE:
<221> NAME/KEY: misc_feature
<222> LOCATION: (47)..(47)
<223> OTHER INFORMATION: n = a nonstandard nucleotide of the instant
      invention
<220> FEATURE:
<221> NAME/KEY: misc_feature
<222> LOCATION: (48)..(48)
<223> OTHER INFORMATION: n = a nonstandard nucleotide of the instant
      invention
<220> FEATURE:
<221> NAME/KEY: misc_feature
<222> LOCATION: (49)..(49)
<223> OTHER INFORMATION: n = a nonstandard nucleotide of the instant
      invention

<400> SEQUENCE: 11
ctantccncc ancnancgga catcaagcag ccatgcaaat gttaannnng                 50

<210> SEQ ID NO 12
<211> LENGTH: 35
<212> TYPE: DNA
<213> ORGANISM: Artificial Sequence
<220> FEATURE:
<223> OTHER INFORMATION: Synthetic

<400> SEQUENCE: 12
tgctatgtca cttcccttg gttctctcat ctggc                                  35
```

```
<210> SEQ ID NO 13
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (31)..(31)
<223> OTHER INFORMATION: n = a nonstandard nucleotide of the instant
      invention
<220> FEATURE:
<221> NAME/KEY: misc_feature
<222> LOCATION: (32)..(32)
<223> OTHER INFORMATION: n = a nonstandard nucleotide of the instant
      invention
<220> FEATURE:
<221> NAME/KEY: misc_feature
<222> LOCATION: (33)..(33)
<223> OTHER INFORMATION: n = a nonstandard nucleotide of the instant
      invention
<220> FEATURE:
<221> NAME/KEY: misc_feature
<222> LOCATION: (34)..(34)
<223> OTHER INFORMATION: n = a nonstandard nucleotide of the instant
      invention

<400> SEQUENCE: 13
tgctatgtca cttccccttg gttctctcat nnnnc                               35

<210> SEQ ID NO 14
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: n = a nonstandard nucleotide of the instant
      invention
<220> FEATURE:
<221> NAME/KEY: misc_feature
<222> LOCATION: (8)..(8)
<223> OTHER INFORMATION: n = a nonstandard nucleotide of the instant
      invention
<220> FEATURE:
<221> NAME/KEY: misc_feature
<222> LOCATION: (12)..(12)
<223> OTHER INFORMATION: n = a nonstandard nucleotide of the instant
      invention
<220> FEATURE:
<221> NAME/KEY: misc_feature
<222> LOCATION: (14)..(14)
<223> OTHER INFORMATION: n = a nonstandard nucleotide of the instant
      invention
<220> FEATURE:
<221> NAME/KEY: misc_feature
<222> LOCATION: (16)..(16)
<223> OTHER INFORMATION: n = a nonstandard nucleotide of the instant
      invention
<220> FEATURE:
<221> NAME/KEY: misc_feature
<222> LOCATION: (48)..(48)
<223> OTHER INFORMATION: n = a nonstandard nucleotide of the instant
      invention
<220> FEATURE:
<221> NAME/KEY: misc_feature
<222> LOCATION: (49)..(49)
<223> OTHER INFORMATION: n = a nonstandard nucleotide of the instant
      invention
<220> FEATURE:
<221> NAME/KEY: misc_feature
<222> LOCATION: (50)..(50)
<223> OTHER INFORMATION: n = a nonstandard nucleotide of the instant
      invention
```

```
<220> FEATURE:
<221> NAME/KEY: misc_feature
<222> LOCATION: (51)..(51)
<223> OTHER INFORMATION: n = a nonstandard nucleotide of the instant
      invention

<400> SEQUENCE: 14
cagnaagngg tngntngtgc tatgtcactt ccccttggtt ctctcatnnn nc          52
```